(12) United States Patent
Ziv et al.

(10) Patent No.: US 8,101,666 B2
(45) Date of Patent: Jan. 24, 2012

(54) METHODS AND COMPOUNDS FOR DETECTION OF MEDICAL DISORDERS

(75) Inventors: Ilan Ziv, Kfar Saba (IL); Anat Shirvan, Herzliya (IL)

(73) Assignee: Aposense Ltd., Petach-Tikva (IL)

(*) Notice: Subject to any disclaimer, the term of this patent is extended or adjusted under 35 U.S.C. 154(b) by 1421 days.

(21) Appl. No.: 11/631,490

(22) PCT Filed: Jul. 7, 2005

(86) PCT No.: PCT/IL2005/000725
§ 371 (c)(1),
(2), (4) Date: Jan. 4, 2007

(87) PCT Pub. No.: WO2006/006156
PCT Pub. Date: Jan. 19, 2006

(65) Prior Publication Data
US 2007/0232702 A1    Oct. 4, 2007

Related U.S. Application Data

(60) Provisional application No. 60/585,852, filed on Jul. 8, 2004.

(51) Int. Cl.
*A01N 33/02* (2006.01)
*A61K 31/135* (2006.01)
*C07C 211/00* (2006.01)

(52) U.S. Cl. ........ 514/646; 514/647; 514/648; 514/649; 514/650; 564/305; 564/306; 564/307; 564/308

(58) Field of Classification Search .......... None
See application file for complete search history.

(56) References Cited

U.S. PATENT DOCUMENTS
4,477,498 A    10/1984    Deiner et al.

FOREIGN PATENT DOCUMENTS

| CA | 1 292 733 | | 12/1991 |
|----|-----------|---|---------|
| WO | WO 02/057222 | | 7/2002 |
| WO | WO 2004/096120 | | 11/2004 |
| WO | WO 2005/053752 | | 6/2005 |
| WO | WO2005053752 | * | 6/2005 |

OTHER PUBLICATIONS

Seiler, N. Determination of Amines and Amino Acids as 1-Dimethylaminonaphthalene-5-Sulfonamides on Thin Layer Chromatography. 1966, vol. 220 No. 2, pp. 109-27.
International Search Report for Application No. PCT/IL05/00725 mailed Sep. 21, 2006.
Supplementary European Search Report for European Application No. EP 05 75 8946 Date of completion of the search Nov. 3, 2008.
XP 002502137—Seiler, N. Determination of amines and amino acids as 1-dinethylaminonapthalene-5-sulfonamides on thin layer chromatography. 1966. vol. 220 No. 2, pp. 109-27.
XP 002502235—Database Biosis (online) Biosciences Information Service, Philadelphia, PA, US. Apr. 2003 Muezzinoglu Aysen: "A study of volatile organic sulfur emissions causing urban odors." vol. 51, No. 4, pp. 245-252.

* cited by examiner

*Primary Examiner* — Alton Pryor
(74) *Attorney, Agent, or Firm* — Pearl Cohen Zedek Latzer, LLP

(57) ABSTRACT

The invention provides methods for detection of medical disorders, associated with cellular oxidative stress, cell degeneration and/or cell death. The invention further relates to compounds comprising a thiol (—SH) group, for detecting cells undergoing oxidative stress, degeneration and/or a death process. The invention further provides methods for utilizing the compounds in medical practice, for diagnostic and therapeutic purposes.

14 Claims, 6 Drawing Sheets

A

B

A

B

A

B

A

B

A

B

METHODS AND COMPOUNDS FOR DETECTION OF MEDICAL DISORDERS

This application is a National Phase application of PCT International Application No. PCT/IL2005/000725, International Filing Date: Jul. 7, 2005, claiming priority from U.S. Provisional Patent Application Ser. No. 60/585,852, entitled "METHODS AND COMPOUNDS FOR DETECTION OF NEUROLOGICAL DISORDERS" filed Jul. 8, 2004, all of which are incorporated by reference in their entirety.

FIELD OF THE INVENTION

The invention provides methods for detection of medical disorders, associated with cellular oxidative stress, cell degeneration and/or cell death. The invention further relates to compounds comprising a thiol (—SH) group, for detecting cells undergoing oxidative stress, degeneration and/or a death process. The invention further provides methods for utilizing the compounds in medical practice, for diagnostic and therapeutic purposes.

BACKGROUND OF THE INVENTION

Accurate diagnosis of various neurological disorders, and especially neurodegenerative disorders such as Alzheimer's disease, Parkinson's disease, amyotrophic lateral sclerosis (ALS), Huntington's disease, Creutzfeldt-Jacob disease or progressive supranuclear palsy (PSP), and specifically in the early stages of disease, is often a substantial challenge for the clinical neurologist. The tools available for the clinical neurologist for that purpose comprise the patient's medical history, the reported symptoms, the findings in the neurological examination and ancillary examinations, such as brain computerized tomography (CT scan) or magnetic resonance imaging (MRI). Taken together, currently these tools are often insufficient, and are often capable of reflecting the underlying neuropathological processes only at relatively late stages of disease. Another challenge often encountered in the clinical neurological practice is the monitoring of response of brain tumors to treatment. Therefore, in order to make an accurate diagnosis, to devise therapy, to follow disease course or to assess the effect of treatment in any of the above serious and debilitating neurological disorders, there is therefore clearly a need for novel, non-invasive methods, for detection and imaging of neuropathological processes.

Molecular imaging is a novel and rapidly-developing field, concerning the use of molecular probes, comprising a marker for imaging, which can report via non-invasive clinical imaging procedures, such as positron emission tomography (PET scan), on cellular processes associated with health and disease. Oxidative stress is one of the hallmarks in the pathogenesis of many medical disorders. Cellular damage due to oxygen free radicals has been shown to play an important role in neurodegeneration. Apoptosis is linked to oxidative stress both at the level of triggering of the death process, since oxidative stress is a potent inducer of the death program; and at the level of execution of cell death, as dramatic alterations in mitochondrial function, and breakdown of cellular antioxidant mechanisms are universally encountered during apoptosis. To date, there is no tool in clinical practice for molecular imaging of oxidative stress.

SUMMARY OF THE INVENTION

In an embodiment of the invention, there is provided a method for detection of cell death or a disease process associated with oxidative stress in a tissue of a patient or animal, comprising: (i) administering to the patient or animal a thiol-containing compound of the invention, linked to a marker for imaging; and (ii) detecting the amount of compound bound to the examined tissue of the patient or animal; wherein detection of a significant amount of the compound bound to the tissue of the patient or animal indicates the existence of cell death or a disease process in said tissue.

In another embodiment of the invention, there is provided a method for detection of cell death or a disease process associated with oxidative stress in the nervous system of an examined patient or animal, comprising: (i). administering a to the patient or animal a thiol-containing compound of the invention linked to a marker for imaging; and (ii) detecting the amount of compound bound to the examined part of the nervous system; wherein detection of a significant amount of the compound bound to the examined part of the nervous system, as compared with control, indicates the existence of cell death or a disease process within said part of the nervous system.

In an embodiment of the invention, oxidative stress refers to damage to biological tissues that occurs when there is an excess of free radicals, a decrease in antioxidant levels, or both.

In another embodiment of the invention, the disease process to be detected by the compounds and methods of the invention is associated with oxidative stress within neuronal or glial cells; neuronal or glial cells undergoing apoptosis; neuronal or glial cells undergoing other modes of cell death; processes of neuronal degeneration, which may be degeneration of either neuronal cell bodies or neurites; cells of a brain tumor undergoing a death process (e.g., by apoptosis), and abnormal accumulation of proteins within or associated with cells of the nervous system. Such abnormal accumulation of proteins can be, among others, in the form of intracellular inclusion bodies (e.g., neurofibrillary tangles, Lewy bodies) or in the form of extracellular abnormal protein deposits (e.g., amyloid plaques).

In another embodiment of the invention, the method of the invention is used for the diagnosis of a neurological disorder which may be an acute injury, such as without limitation, cerebral stroke, toxic insults or brain trauma, or a chronic neurodegenerative disorder, such as without being limited, Alzheimer's disease, Parkinson's disease, amyotrophic lateral sclerosis (ALS), multi-system atrophy (MSA), progressive supranuclear palsy (PSP), Huntington's disease, Lewy body disease, prion disorders such as Creutzfeldt-Jacob disease, and demyelinative disorders such as multiple sclerosis.

In another embodiment of the invention, the method of the invention is used for monitoring of response of tumors to therapy. Since most anti-tumor agents, such as chemotherapeutic drugs or irradiation act through induction of apoptosis within the tumor, imaging via the methods and compounds of the invention of the level of tumor cell death induced by therapy, can teach in a non-invasive manner on the efficacy of the anti-tumor treatment.

In an embodiment of the invention, the compound used in the invention, which serves for the detection of cells undergoing a disease process or a cell death process within a tissue or organ, has the following formula (I):

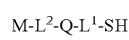

wherein $L^1$ is selected from $C_1$, $C_2$, and $C_3$ linear or branched alkylene; $L^2$ is selected from null and a $C_1$, $C_2$, $C_3$, $C_4$, $C_5$, $C_6$ linear or branched alkylene linker; Q is selected from null, and optionally substituted aryl, heteroaryl, aryl-sulfonamide and heteroaryl-sulfonamide; and M is a marker for imaging.

In another aspect, the invention provides compounds and uses thereof for in the detection of cell death in a tissue or organ, having the structure set forth in formula (II):

(II)

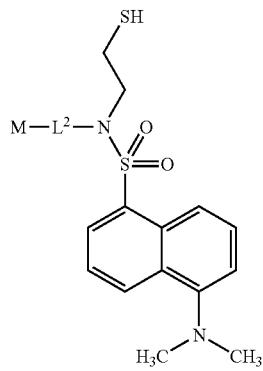

wherein M and L² are each as defined above.

In another embodiment of the invention, M is hydrogen and L² is null, the compound is designated NST729, and it has the structure set forth in formula III:

(III)

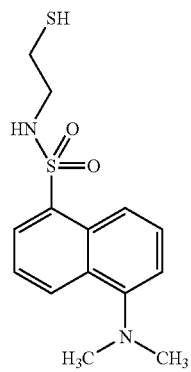

In another aspect of the invention, there is provided a compound, represented by the structure set forth in formula IV:

(IV)

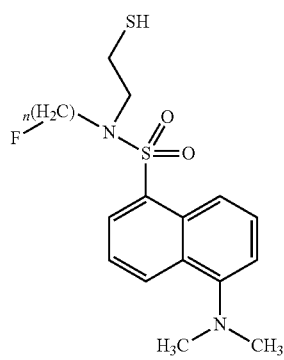

wherein the n stands for an integer of 2 or 3, and the F atom being either ¹⁸F or ¹⁹F.

In the case that n=3, the compound is designated NST739.

In another aspect of the invention, there is provided a compound represented by the structure set forth in formula V:

(V)

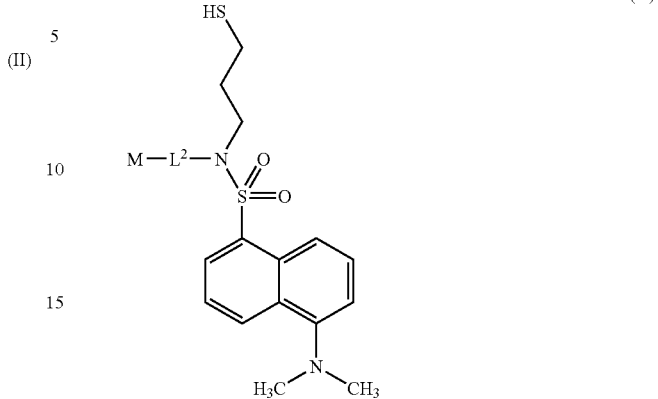

wherein M and L² are each as defined above. In an embodiment of the invention, M is hydrogen and L² is null.

In another aspect of the invention, there is provided a compound represented by the structure set forth in formula VI:

(VI)

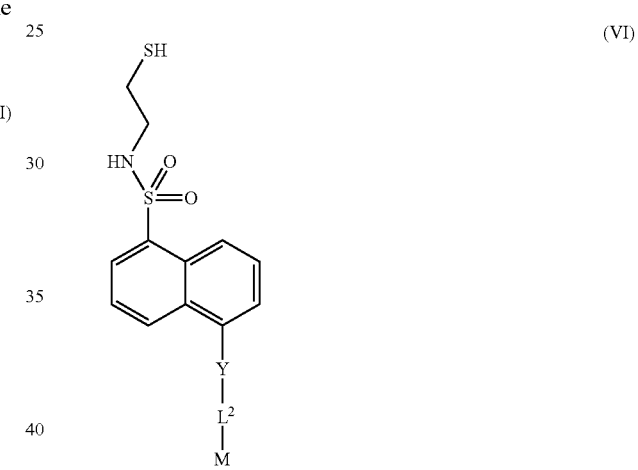

wherein L² and M have the same meaning as above; and Y is selected from null, —O—, NH, and $C_1$, $C_2$, $C_3$, or $C_4$ alkylamine.

In another embodiment of the invention, there is provided a compound, represented by the structure set forth in formula VII:

(VII)

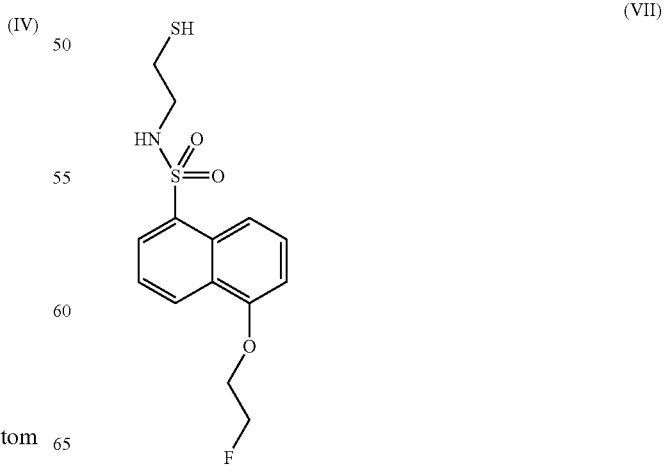

wherein the F atom can be either ¹⁸F or ¹⁹F.

In another aspect of the invention, there is provided a compound represented by the structure set forth in formula VIII:

(VIII)

wherein F can be either $^{18}$F or $^{19}$F, R is aryl or heteroaryl, $C_1, C_2, C_3, C_4, C_5, C_6$, linear or branched, optionally substituted alkyl, or combinations thereof.

In another aspect of the invention, there is provided a compound represented by the structure set forth in formula IX:

(IX)

wherein F can be either $^{18}$F or $^{19}$F

The compounds used in the invention also include pharmaceutically-acceptable salts, metal chelates, solvates and hydrates of the compounds, as well as solvates and hydrates of the pharmaceutically-acceptable salts. Examples of pharmaceutically-acceptable addition salts include inorganic and organic acid addition salts such as, for example without being limited, hydrochloride, hydrobromide, phosphate, sulphate, citrate, lactate, tartrate, maleate, fumarate, mandelate, oxalate, and acetate. Alternatively, pharmaceutically-acceptable inorganic and organic base addition salts may be used such as sodium hydroxide, potassium hydroxide, lithium hydroxide, and the like.

In another embodiment of the invention, there is provided a method of detecting of oxidative stress or cell death within a brain tumor of a patient or animal, comprising the steps of administering to the patient or animal any one of the compounds represented by any of the structures set forth in formulae I-IX; and detecting the amount of compound bound to brain tumor, wherein detection of a significant amount of the compound bound to brain tumor indicates the existence of oxidative stress or cell death within the tumor In another embodiment of the invention, there is provided use of the compounds represented by any of the structures set forth in formulae I-IX for the manufacture of a diagnostic composition for detection of cell death or a disease process in a tissue of a patient or animal.

In an embodiment of the invention, the tissue may be the brain or a part thereof.

DETAILED EMBODIMENTS OF THE INVENTION

The invention is based, in one of its embodiment, on the observation, that the redox state of thiol (—SH) groups of cysteines of cellular proteins can serve as a measure for distinguishing between normal healthy cells and cells undergoing disease-related processes associated with oxidative stress, or cells undergoing a death process such as apoptosis, or for the detection of abnormal deposits of proteins, such as amyloid plaques within the brain tissue. The thiol groups of cysteine residues of intracellular proteins of healthy cells are mostly in a reduced state i.e., being free thiols (—SH). This is due to the high cytosolic concentrations of —SH-reducing agents in the viable, healthy cells. By contrast, in situations of cell disease or cell death such as apoptosis, cells encounter oxidative stress and lose intracellular antioxidant mechanisms. This is reflected, among others, by occurrence of disulfide bonds (S—S) between thiol groups of cysteines of intracellular proteins.

Figure 6:
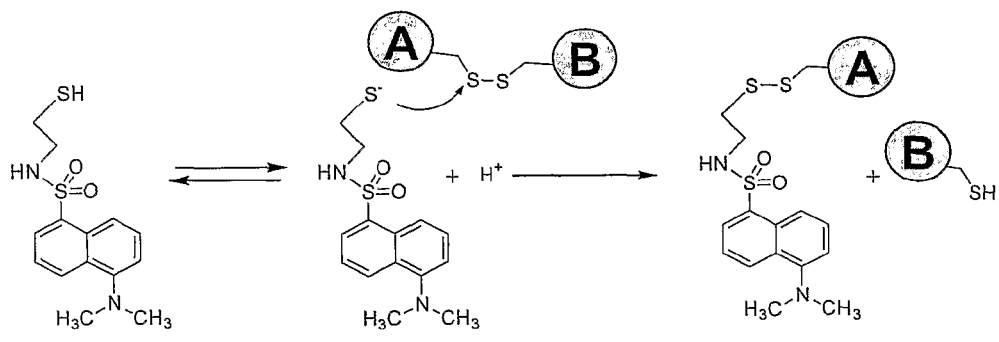
FIG. 6 shows the mechanism of selective binding of the compounds of the invention to cells undergoing a disease associated with oxidative stress, or a death process. Binding of NST729 to intracellular proteins of a cell undergoing apoptosis is illustrated. (A). Binding of NST729 to proteins in the cytosol of a cell undergoing apoptosis; (B). Lack of binding of NST729 in the cytosol of a healthy cell. A and B in the figures are examples of intracellular proteins.
Figure 6:
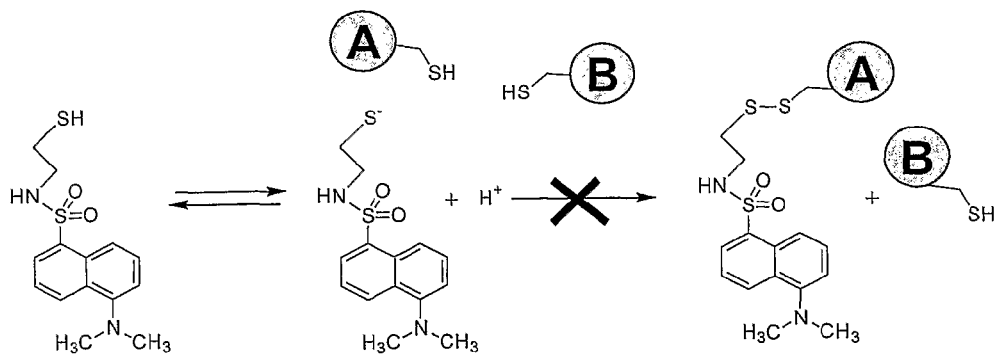

The invention concerns methods for detection of cellular disease processes or cell death via characterization of the load of disulfide bonds within the cells of the examined tissue or organ. The characterization of cellular load of disulfide bonds, according to the methods of the invention, is based on a novel concept, of utilization in vivo of thiolate-disulfide reaction (TDR) for this purpose. The TDR is a chemical reaction between a disulfide bond and a thiolate anion, by which a sulfur atom of the S—S bond is being substituted by the attacking thiolate group. In one its aspects, the invention concerns administration of a compound, comprising both a thiol group and a marker for imaging. The thiol group, in the form of thiolate, will interact with disulfides via the TDR, resulting in linkage of the marker for imaging to the site via S—S bond (FIG. 6). Unbound compound will be washed out of the examined cells. Thus, sites of occurrence of disulfide bonds will be reported and monitored by imaging modalities, respective of the marker chosen for imaging. Since, as described above, occurrence of intracellular disulfide bonds is associated with cell disease or cell death, the image obtained will correspond to the occurrence of these disease-related processes within the examined tissue, thus informing on their extent.

In an embodiment of the invention, there is provided a method for the detection of a disease process or cell death within a tissue of a patient or animal, comprising: (i) administering a thiol-containing compound of the invention, linked to a marker for imaging; and (ii) detecting the amount of compound bound to the tissue of the patient or animal; wherein detection of a significant amount of the compound bound to the tissue of the patient or animal indicates the existence of cell death or a disease process in the tissue.

In an embodiment of the invention, there is provided a method for detection of a disease process within the nervous system of an examined patient or animal, comprising: (i). administering a thiol-containing compound of the invention, linked to a marker for imaging; and (ii). detecting the amount of compound bound to the examined part of the nervous system; wherein detection of a significant amount of the compound bound to the examined part of the nervous system, as compared with control, indicates the existence of a disease process within said part of the nervous system.

The term "significant amount of the compound bound to the part of the nervous system" refers, according to the embodiments of the invention, to the amount of the compound of the invention, comprising or is being attached to a marker for diagnostics, which binds to the part of the nervous system in an amount which is at least 10% greater than the amount bound to a normal, not diseased, part of the nervous system. The detection may be in vivo, by using imaging techniques or in vitro, or ex vivo, by using methods for visualizing the tissue. In another embodiment, the amount may be higher by 50%. In another embodiment of the invention, the amount may be higher by 75%. In another embodiment, the amount may be higher by 150%. In another embodiment, the amount may be higher by about two fold. In another embodiment, the amount may be higher than at least five fold. In another embodiment, the amount may be higher by at least ten fold.

The term "disease process" refers hereinafter to any process within cells or tissues, that impairs the function or survival of said cells or tissues and is associated with oxidative stress. Disease processes according to the invention may involve inter-alia the nervous system.

The term "cell death" refers hereinafter to any process leading to the demise of cells, being among others, cell death by apoptosis or necrosis.

In another embodiment of the invention, the disease process to be detected by the compound and methods of the invention is oxidative stress within neuronal or glial cells; neuronal or glial cells undergoing apoptosis; neuronal or glial cell death undergoing other modes of cell death; processes of neuronal degeneration, which may be degeneration of either cell bodies or neurites; cells of a brain tumor undergoing a death process (e.g., by apoptosis), and abnormal accumulation of proteins within or associated with cells of the nervous system. Such abnormal accumulation of proteins can be, among others, in the form of intracellular inclusion bodies (e.g., neurofibrillary tangles, Lewy bodies) or in the form of extracellular abnormal protein deposits (e.g., amyloid plaques).

In another embodiment of the invention, the method and compounds described herein may be used for the diagnosis of a neurological disorder which may be an acute injury, such as without limitation, cerebral stroke, toxic insults or brain trauma, or a chronic neurodegenerative disorder, such as without being limited, Alzheimer's disease, Parkinson's disease, amyotrophic lateral sclerosis (ALS), multi-system atrophy (MSA), progressive supranuclear palsy (PSP), Huntington's disease, Diffuse Lewy body disease, prion disorders such as Creutzfeldt-Jacob disease, and demyelinative disorders such as multiple sclerosis.

In another embodiment of the invention, the method of the invention is used for monitoring of response of brain tumors to therapy. Since most anti-tumor agents, such as chemotherapeutic drugs or irradiation act through induction of apoptosis within the tumor, imaging via the methods and compounds of the invention of the level of tumor cell death induced by therapy, can teach in a non-invasive manner on the effect of therapy on the tumor.

In an embodiment of the invention, the compound used in the invention, which serve for the detection of cells undergoing a disease process or a cell death process within a tissue or organ, has the following formula (I):

M-L$^2$-Q-L$^1$-SH

Wherein L$^1$ is selected from $C_1$, $C_2$, and $C_3$ linear or branched alkylene; L$^2$ is selected from null and a $C_1$, $C_2$, $C_3$, $C_4$, $C_5$, $C_6$ linear or branched alkylene linker; Q is selected from null, and optionally substituted aryl, heteroaryl, arylsulfonamide and heteroaryl-sulfonamide; and M is selected from hydrogen and a marker for imaging.

In an embodiment of the invention, the marker for imaging (M) may be selected from $^{18}$F, $^{15}$O, $^{18}$O, $^{11}$C, $^{13}$C, $^{124}$I, $^{13}$N and $^{75}$Br.

In another aspect, the invention provides compounds and uses thereof for the detection of cell death in a tissue or organ, having the structure set forth in formula (II):

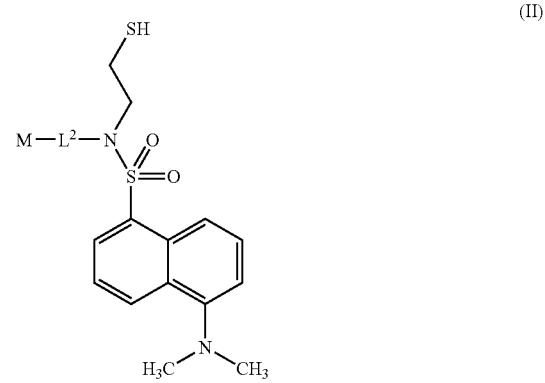

(II)

wherein M and L$^2$ are each as defined above.

In another embodiment of the invention, M is hydrogen and L$^2$ is null, the compound is designated NST729, and it has the structure set forth in formula III:

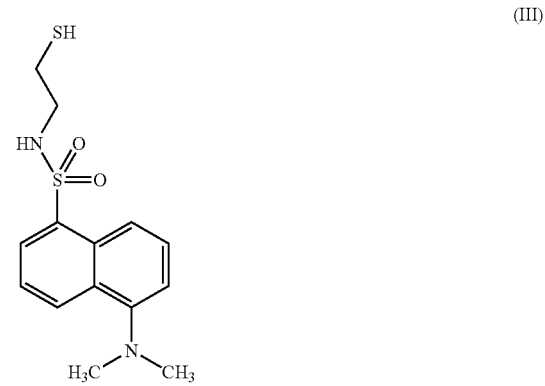

(III)

In another aspect of the invention, there is provided a compound, represented by the by the structure set forth in formula IV:

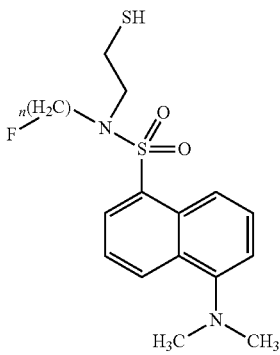

(IV)

wherein the n stands for an integer of 2 or 3, and the F atom being either $^{18}$F or $^{19}$F. In the case that n=3, the compound is designated NST739.

In another aspect of the invention, there is provided a compound represented by the structure set forth in formula V:

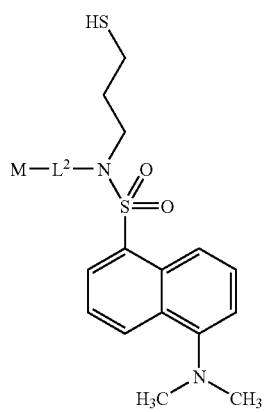

(V)

wherein M and L$^2$ are each as defined above. In an embodiment of the invention, M is hydrogen and L$^2$ is null.

In another aspect of the invention, there is provided a compound represented by the structure set forth in formula VI:

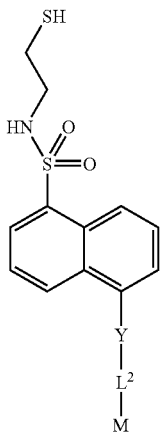

(VI)

wherein L$^2$ and M have the same meaning as above; and Y is selected from null, —O—, NH, and C$_1$, C$_2$, C$_3$, or C$_4$ alkylamine.

In another embodiment of the invention, there is provided a compound, represented by the structure set forth in formula VII:

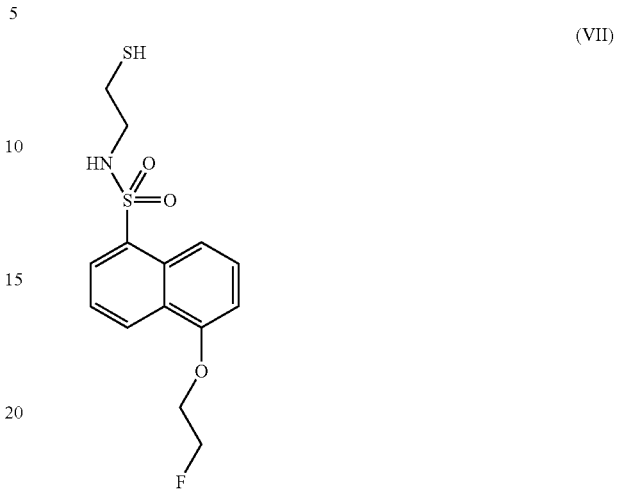

(VII)

wherein the F atom can be either $^{18}$F or $^{19}$F.

In another aspect of the invention, there is provided a compound represented by the structure set forth in formula VIII:

(VIII)

wherein F can be either $^{18}$F or $^{19}$F, R is aryl or heteroaryl, C$_1$, C$_2$, C$_3$, C$_4$, C$_5$, C$_6$, linear or branched, optionally substituted alkyl, or combinations thereof. In another aspect of the invention, there is provided a compound represented by the structure set forth in formula IX:

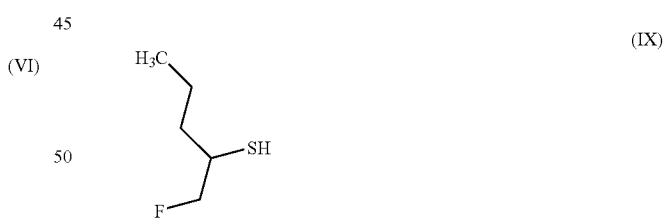

(IX)

wherein F can be either $^{18}$F or $^{19}$F

The compounds used in the invention also include pharmaceutically-acceptable salts, metal chelates, solvates and hydrates of the compounds, as well as solvates and hydrates of the pharmaceutically-acceptable salts. Examples of pharmaceutically-acceptable addition salts include inorganic and organic acid addition salts such as, for example without being limited, hydrochloride, hydrobromide, phosphate, sulphate, citrate, lactate, tartrate, maleate, fumarate, mandelate, oxalate, and acetate. Alternatively, pharmaceutically-acceptable inorganic and organic base addition salts may be used such as sodium hydroxide, potassium hydroxide, lithium hydroxide, and the like.

The compounds of the invention may distinguish between normal healthy cells, and cells undergoing a disease-related process, being inter alia, cells undergoing oxidative stress, cells undergoing a death process such as apoptosis, neurites undergoing degeneration, or abnormal accumulation of proteins within or associated with cells of the nervous system, being among others, in the form of intracellular inclusion bodies (e.g., neurofibrillary tangles, Lewy bodies) or in the form of extracellular abnormal protein deposits (e.g., amyloid plaques).

While intracellular proteins of healthy cells are characterized by reduced state of thiol groups (i.e., being in the form of free thiols), due to the strong intracellular anti-oxidant mechanisms, the above pathologies are characterized by loss of said anti-oxidant mechanisms, thus favoring formation of disulfide (—S—S—) bonds. The thiol group of any compound of the invention is prone to participation in these disulfide bond formation reactions, and thus the compound will bind to the cells, in an extent directly correlated with the extent of loss of cellular anti-oxidant mechanisms. Therefore, the level of binding of the compound of the invention to the examined cell reports on the level of impairment of its cellular redox state, associated with the disease or death process of said cell. In addition, the relatively low molecular weight, and hydrophobicity in physiological pH allows the compounds of the invention to efficiently cross the blood-brain-barrier (BBB) and access the brain cells.

The method of detection neuropathological processes in the invention, as was shown in Example 4, may be used as a tool for measuring the amount of amyloid plaques in brain of a subject suspected of having Alzheimer's disease. Accordingly, there is provided a method of measuring the amount of amyloid plaques in brain of a subject suspected of having brain amyloidosis, comprising the steps of: (i) contacting a brain tissue with any of the compounds according to the structure set forth in formulae I-IX, including the definitions as described above; and (ii) imaging the human or animal, so as to determine the amount of the compound bound to plaques in the brain tissue.

The above mentioned method may also be applied for identifying the efficacy of an agent administered to reduce the amount of amyloid plaques in a patient or in a animal, the latter may be, in one embodiment, a transgenic animal, comprising the steps of: (i) administering the agent to the animal, (ii) administering any of the compounds according to the structures set forth in formulae I-IX, including the definitions as described above and (iii) detecting the signal by imaging or by histopathology, wherein if the image intensity is reduced, or if the amount of the detected plaques is reduced, the agent is identified as efficient in reducing the load of the amyloid plaques in the examined brain. It is noted that steps (i) and (ii) may be changed in their order.

In another embodiment of the invention, there is provided a method for detecting pathological alterations in the brains of people suspected of suffering from acute neurological disorders, such as cerebral stroke, toxic insults or brain trauma, or chronic neurodegenerative disorders such as Alzheimer's disease, Parkinson's disease, amyotrophic lateral sclerosis (ALS), multi-system atrophy (MSA), progressive supranuclear palsy (PSP), Huntington's disease, Lewy body disease, prion disorders such as Creutzfeldt-Jacob disease, and demyelinative disorders such as multiple sclerosis. The respective neuropathological alterations are selected from cells undergoing a disease process, cells undergoing a death process such as apoptosis, neurites undergoing deformation and degeneration, and intra- or extra-cellular protein deposits within the brain tissue, such as amyloid plaques. The method comprises the steps of: (i) contacting the brain tissue with a any of the compounds according to the structure set forth in formulae I-IX, including the definitions as described above; and (ii) imaging the subject so as determine the amount of the compound bound the brain tissue, wherein imaging of binding of a significant amount to the examined brain in comparison to control indicates brain pathology.

In another embodiment of the invention, there is provided a method of detecting the efficacy of an agent in reducing any of the above neuropathogical alterations in a patient or in a animal, the latter may be, in one embodiment a transgenic animal, said method comprising the steps of: (i) administering the agent to the examined patient or animal; (ii) administering any of the compounds according to the structures set forth in formulae I-IX, including the definitions as described above; and (iii) detecting the signal by imaging, wherein if the signal intensity is reduced, the agent is identified as efficient in reducing the load of disease in the examined brain. It is noted that steps (i) and (ii) may be changed in their order.

In an embodiment of the invention, relating to the use of the compounds of the invention for obtaining images of cells or tissue undergoing a disease process in a patient via radionuclide imaging by PET or SPECT, the calculation of the ratio between the amount of the compound bound to the abnormal tissue vs. the amount bound to the normal cells may be conducted by comparing the amplitude or intensity of the signal obtained from the tissue inflicted by the death process, with the amplitude/intensity of the signal obtained from a tissue not-inflicted by the process.

In one embodiment of the invention, there is provided a compound which selectively targets a cell undergoing a death process, such as for example, a cell undergoing apoptosis, wherein the compound is represented by the structure set forth in formulae I-IX.

In another aspect of the invention, there is provided a method of detecting a cell undergoing a death process within a cell population, the method comprising: (i). contacting the cell population with a compound represented by any one of the structure set forth in formulae I-IX, or pharmaceutically acceptable salts, metal chelates, solvates and hydrates of the compound represented by the structure as set forth in formulae I-IX, and solvates and hydrates of the salts; and (ii). determining the amount of the compound bound to the cells, wherein a significant amount of compound bound to a cell indicates its being a cell undergoing a death process.

The term "significant amount of the compound bound to a cell" refers according to the invention to the amount of the compound of the invention, comprising or is being attached to a marker for diagnostics, which binds to a cell undergoing a death process in an amount which is at least 10% greater than the amount bound to a normal cell. In another embodiment, the amount may be higher by 50%. In another embodiment of the invention, the amount may be higher by 75%. In another embodiment, the amount may be higher by 150%. In another embodiment the amount may be higher by about two fold. In another embodiment the amount may be higher than at least two fold. In another embodiment, the amount may be higher than at least five fold. In another embodiment, the amount may be higher by at least ten fold.

According to another aspect of the invention, there is provided a method for detecting of cells undergoing death process in a patient or an animal, the method comprising: (i) administering to the patient or animal a compound a compound represented by the structure set forth in formulae I-IX, wherein the compound comprises a marker for imaging, such as $^{18}$F or pharmaceutically acceptable salts, metal chelates, solvates and hydrates of the compound represented by the structure as set forth in formulae I-IX and solvates and hydrates of the salts; and (ii) imaging the examined patient or animal, so as to determine the amount of compound bound to cells, wherein detection of a significant amount of compound bound to cells indicates that these cells are cells undergoing death process.

The compounds of the invention may be used for selective targeting of medicinally-useful agents to tissues and organs comprising cells undergoing death process, in two different approaches of the invention:

(i). According to a first approach, termed hereinafter the "detection approach", the selective binding may be utilized to targeting a marker for imaging to cells undergoing death process. This may be used in clinical practice, either in vivo, ex vivo or in vitro, for the diagnosis of diseases in which such cells emerge, as will be explained herein below.

(ii). According to a second approach, termed hereinafter the "therapeutic approach", the property of selective binding is used for selective targeting of therapeutic agents to organs and tissues in the body wherein cells undergoing death process emerge, e.g., regions of cell death, thrombus formation or inflammation.

The compounds of the invention may be used for the detection and diagnosis of a wide variety of medical conditions, characterized by formation cells undergoing death process. Examples of clinical conditions characterized by cells undergoing death process are as follows:

Diseases which are characterized by occurrence of excessive apoptosis, such as degenerative disorders, neurodegenerative disorders (e.g., Parkinson's disease, Alzheimer's disease, Huntington chorea), AIDS, ALS, Prion Diseases, myelodysplastic syndromes, ischemic or toxic insults, graft cell loss during transplant rejection; tumors, and especially highly malignant/aggressive tumors, are also often characterized by enhanced apoptosis in addition to the excessive tissue proliferation.

Inflammatory disorders, and/or diseases associated with immune-mediated etiology or pathogenesis, auto-immune disorders such as antiphospholipid antibody syndrome, systemic lupus erythematosus, connective tissue disorders such as rheumatoid arthritis, scleroderma; thyroiditis; dermatological disorders such as pemphigus or erythema nodosum; autoimmune hematological disorders; autoimmune neurological disorders such as myasthenia gravis; multiple sclerosis; inflammatory bowel disorders such as ulcerative colitis; vasculitis.

Atherosclerotic plaques, and especially plaques that are unstable, vulnerable and prone to rupture, are also characterized by Cells undergoing death process, such as apoptotic macrophages, apoptotic smooth muscle cells, apoptotic endothelial cells, and activated platelets. Such activated platelets are encountered in the thrombi, often associated with the unstable atherosclerotic plaque.

In one of its embodiments, the present invention concerns a pharmaceutical composition comprising as an effective ingredient any of the compounds described in the invention, comprising or linked to a marker for imaging, for the detection of neural tissue disease or a death process or amyloid plaques either in vitro, ex vivo or in vivo. Then, the detectable label can be detected by any manner known in the art and in accordance with the specific label used, for example, fluorescence, radioactive emission, color production, magnetic resonance, x-ray and the like. The imaging will be performed utilizing the appropriate equipment according to the tracer and the imaging modality used, as known to those in the art.

In one embodiment, the detectable label may a radio-isotope. Examples for a radio-isotope, to be used for positron emission tomography (PET) scan are $^{18}F$, $^{15}O$, $^{18}O$, $^{11}C$, $^{13}C$, $^{124}I$, $^{13}N$ and $^{75}Br$.

In an embodiment, the compound of the invention is aimed at clinical imaging via PET scan, and the compound comprises $^{18}F$ atom(s).

The method for labeling the compound, which can be any compound of the structures described above, with $^{18}F$ for PET imaging, comprises the step of attaching an $^{18}F$ atom to the compound; thereby radio-labeling a compound with $^{18}F$ for PET imaging. Optionally, during the reaction of radio-labeling with the $^{18}F$ atom, the other functional groups of the compound (e.g., the thiol group) may be protected by appropriate protecting groups prior to the step of attaching $^{18}F$ atom, wherein said protecting groups are being removed after the step of attachment of the $^{18}F$ atom.

For fluorescent detection, the compound of the invention may comprise a fluorescent group as the marker for imaging (i.e., the M group), selected among any fluorescent probe known in the art. Examples for such probes are 5-(dimethylamino) naphthalene-1-sulfonylamide (dansyl-amide), and fluorescein.

The assessment of binding of the compounds to their target sites may be conducted by measuring the fluorescence by FACS or confocal microscopy or by imaging techniques such as PET.

The compounds of the invention may be used for a detection and diagnosis of a wide variety of medical conditions, which are characterized by an oxidative stress, reflected by oxidation of thiol groups of intracellular proteins, with formation of disulfide (—S—S—) bonds, or accumulation of abnormal extracellular protein deposits, e.g., amyloid plaques.

The detection may also be carried out in a person known to have a brain tumor, for the purpose of evaluating the occurrence of oxidative stress and / or cell death within the tumor, occurring either spontaneously, or in response to treatment. Since most anti-tumor treatments, such as chemotherapy or radiotherapy exert their effect by induction of apoptosis, detection by the compounds of the invention of therapy-induced apoptosis of brain tumor cells may teach on the extent of sensitivity of the tumor to the anti-tumor agent. This may substantially shorten the lag period between the time of administration of the anti-cancer treatment and the time of proper assessment of its efficacy, allowing for better optimization of treatment for brain tumors.

The pharmaceutical composition, comprising the compounds of the invention and a pharmaceutically-acceptable carrier may be administered by any of the known routes, inter alia, oral, intravenous, intraperitoneal, intramuscular, subcutaneous, sublingual, intraocular, intranasal or topical administration, or intracerebral administration. The carrier should be selected in accordance with the desired mode of administration, and include any known components, e.g. solvents; emulgators, excipients, talc; flavors; colors, etc. The pharmaceutical composition may comprise, if desired, also other pharmaceutically-active compounds which are used to treat the disease, eliminate side effects or augment the activity of the active component.

EXAMPLES

In order to understand the invention, and to see how it may be carried-out in practice, the following Examples are described: Examples directed to synthesis of the compounds of the invention, and Examples directed to showing the biological performance of the compounds of the invention in selective binding to cells undergoing death process, to senile amyloid plaques and to neurites undergoing degeneration. In the Examples, the compounds comprise a fluorescent label, i.e., a dansylamide group, thus allowing fluorescent microscopy. The selective binding of compounds of the invention to cells undergoing a pathological process was demonstrated in vivo, in several models:

(i). A murine model of cerebral stroke, wherein cell death was induced by occlusion of the middle cerebral artery (MCA);

(ii). Cell death induced by chemotherapy in B-16 murine melanoma;

(iii). Transgenic mice harboring mutated superoxide dismutase gene, thus developing motor neuron-like disease;

(iv). Aged transgenic mice, which have a TG2576 mutation of PAPP, thus developing amyloid plaques within the brain.

The performance of several compounds, comprising a free thiol group is demonstrated: NST728, NST729, NST739 and dansyl-cysteine (DC). n-butyl dansylamide (BDA) was used as a control compound, chosen for its having the same fluorophore and similar molecular weight and hydrorphobicity as the compounds of the invention, yet lacking the —SH group. Therefore, comparison of its performance in the biological studies with the performance of the thiol-containing compounds, teaches the role of said group in entailing the biological activity of the compounds in selective binding to the structure undergoing pathological alterations. Similarly, in the assessment of the performance of dansyl-cysteine (DC) binding to tumors, dansyl-glycine and dansyl-serine were used as control compounds, lacking the thiol group.

The identity of the apoptotic cells was confirmed by TUNEL staining performed on sequential slides; and the identity of the amyloid plaques was confirmed by staining of sequential slides with congo red. Both confirmatory methods are widely acceptable as methods for assessment of apoptosis or detection of amyloid plaques, respectively.

Example 1

Synthesis of NST728, NST729, NST739, DC and BDA

1. Synthesis of dansyl-cysteine (DC)

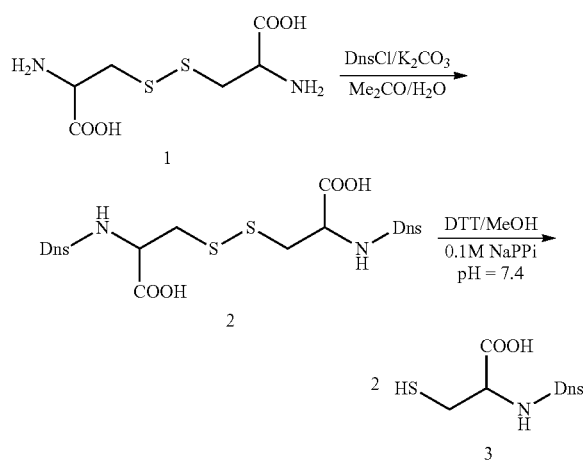

Cystine (1, 1 equivalent) was dissolved in a water/acetone solution with 4 equivalents of potassium carbonate. Dansyl chloride (2.5 equivalents) was added and solution stirred at room temperature for 1.5 hrs. Acetone was removed and solution acidified to pH=3 by adding 2M citric acid. The aqueous mixture was extracted with ethyl acetate. Extracts were combined, dried over magnesium sulfate and solvent evaporated. The crude obtained was dissolved in basic water solution. Solution washed with ether and then reacidified to pH=3 to afford a yellow precipitate. ESI-MS and $^1$H-NMR were consistent with structure 2 [$^1$H-NMR (D$_2$O, δ=ppm): 8.50 (2H, dd); 8.25 (2H, dd); 8.15 (2H, d); 7.50 (4H, m); 7.20 (2H, dd); 4.05 (2H, m); 2.85 (12H, s); 2.60 (4H, m). ESI-MS: Calc. m/z=706.1. Found m/z+H$^+$=707.5].

Intermediate 2 was dissolved in 1:1 methanol:NaPPi buffer (0.1M, pH=7.4). Nitrogen was bubbled through solution for 10 min. and then, 2 equivalents of dithiothreitol (DTT) were added. Reaction was monitored by TLC. More DTT was added when needed. When starting material was consumed, methanol was evaporated and water solution volume reduced to half of it original. Solution was slowly acidified by 2M citric acid to pH=3 and then chilled for 30 min at 0° C. Precipitates were collected by suction filtration, dried on the pump and packaged under nitrogen. ESI-MS and 1H-NMR were consistent with structure 3, i.e., dansyl-cysteine (DC) [$^1$H-NMR (CDCl$_3$, δ=ppm): 8.50 (1H, d); 8.30 (1H, d); 8.20 (1H, d); 7.60 (1H, t); 7.50 (1H, t); 7.20 (1H, d); 5.90 (1H, d); 4.15 (1H, m); 2.90 (6H, s); 2.70 (2H, m). ESI-MS: Calc. m/z=354.4. Found m/z+H$^+$=355.7].

2. Synthesis of NST729

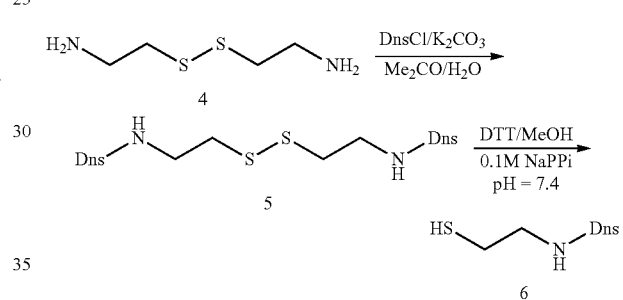

Cystamine (4, 1 equivalent) was dissolved in a water/acetone solution with 4 equivalents of potassium carbonate. Dansyl chloride (2.5 equivalents) was added and solution stirred at room temperature for 1.5 hrs. Acetone was removed and solution acidified to pH=3 by adding 2M citric acid. The aqueous mixture was extracted with ethyl acetate. Extracts were combined, washed with 5% sodium bicarbonate, dried over magnesium sulfate and solvent evaporated. The crude obtained was purified by LC on silica gel. Column was eluted with a gradient of 0-30% ethyl acetate in hexane. Main yellow fluorescent fraction was collected. ESI-MS and $^1$H-NMR were consistent with structure 5, which is Didansyl cystamine: $^1$H-NMR (CDCl$_3$, =ppm): 8.55 (2H, d); 8.23 (4H, dd); 7.50 (4H, q); 7.20 (2H, d); 5.20 (2H, t); 3.10 (4H, q); 2.90 (12H, s); 2.50 (4H, t). ESI-MS: Calc. m/z=618.9. Found m/z+H$^+$=620.1. Intermediate 5 was dissolved in 1:1 methanol:NaPPi buffer (0.1M, pH=7.4). Nitrogen was bubbled through solution for 10 min. and then, 2 equivalents of dithiothreitol (DTT) were added. Reaction was monitored by TLC. More DTT was added when needed. When starting material was consumed, methanol was evaporated and water solution volume reduced to half of it original. Solution was slowly acidified by 2M citric acid to pH=3 and then chilled for 30 min at 0° C. Precipitates were collected by suction filtration, dried on the pump and packaged under nitrogen. ESI-MS and $^1$H-NMR were consistent with structure 6, which is NST729 [n-(2-mercaptoethyl)-dansylamide (6)]: $^1$H-NMR (CDCl$_3$, =ppm): 8.55 (1H, d); 8.30 (2H, t); 7.55 (2H, m); 7.20 (1H, d); 5.20 (1H, d); 3.05 (2H, q); 2.90 (6H, s); 2.50 (2H, q). ESI-MS: Calc. m/z=310.4. Found m/z+H$^+$=311.5.

3. Synthesis of NST n-butyl dansylamide (BDA)

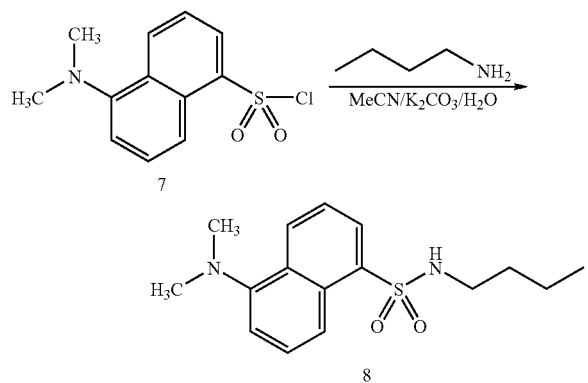

One equivalent of dansyl chloride (7) was added to a solution containing 2 equivalents of both butylamine and potassium carbonate in 1:1 acetonitrile:water. Solution was stirred at room temperature for 1.5 hrs. Acetonitrile was then removed and water residue extracted with ethyl acetate. The organic solution washed with 5% sodium bicarbonate, 2M citric acid and brine. Solution was dried over magnesium sulfate, filtered and solvent removed by flash evaporation. Crude was dissolved in minimal amount of ethyl acetate and hexane was added until cloudiness. Solution was stored in the refrigerator for 2 hrs. The precipitate was collected by suction filtration, washed with hexane and dried on the pump. ESI-MS and $^1$H-NMR were consistent with structure 8, which is (n-butyl dansylamide; BDA): $^1$H-NMR (CDCl$_3$, =ppm): 8.55 (1H, d); 8.30 (2H, dd); 7.55 (2H, m); 7.20 (1H, d); 4.80 (1H, t); 2.90 (8H, m); 1.35 (2H, m). 1.20 (2H, m); 0.70 (3H, t). ESI-MS: Calc. m/z=306.4. Found m/z+H$^+$=307.4.

4. Synthesis of N-(3-fluoropropyl)-N-(2-thioethyl)-dansylamide (NST 739)

n-(2-PMB-thioethyl)-dansylamide (2): 1.3 mmol of 2-aminoethanethiol-PMB ether hydrochloride (1) and 3 mmol of K$_2$CO$_3$ were dissolved in a 1:1 acetonitrile:water mixture. 1 mmol of dansyl chloride was added and solution stirred 20 min. at room temperature. Acetonitrile was removed and the yellow oily residue extracted into DCM from the remaining aqueous phase. The organic extracts were combined and washed with M NaHSO$_4$, dried over MgSO$_4$ and solvent evaporated. TLC (3:2 petroleum ether:ethyl acetate) showed one yellow fluorescent spot at Rf=0.8. $^1$H-NMR and ESI-MS were consistent with intermediate 2. Product was clean enough to be used in next step without further purification. $^1$H-NMR were as follows: (CDCl$_3$, =ppm): 8.55 (1H, d); 8.30 (1H, d); 8.20 (1H, dd); 7.55 (2H, m); 7.20 (1H, d); 7.00 (2H, d); 6.75 (2H, d); 5.20 (1H, t); 3.75 (3H, s); 3.30 (2H, s); 2.95 (2H, q); 2.85 (6H, s); 2.35 (2H, t). ESI-MS: m/z+H$^+$=431.47. 1 mmol of product 2 was dissolved in DMF and stirred 15 min. at 70° C. in presence of 1.5 mmol of Cs$_2$CO$_3$. Then, 1.5 mmol of bromopropanol were added and mixture stirred overnight at 70° C. DMF was removed and residue dissolved in DCM. Solution washed with 1M NaHSO$_4$ and 5% NaHCO$_3$, dried over MgSO$_4$ and solvent removed. TLC (3:2 petroleum ether:ethyl acetate) of crude showed 3 yellow fluorescent spots at Rf=0.46, 0.32 and 0.20 respectively. The crude was purified by flash LC on silica gel. Column was eluted with 25% petroleum ether in DCM until substance at Rf=0.48 was eluted. Then eluent was changed to DCM and the other substances were eluted. Spectral ($^1$H-NMR and ESI-MS) data showed that substance at Rf=0.32 was in accordance with the desired structure 3 which has the following $^1$H-NMR data: (CDCl$_3$, =ppm): 8.55 (1H, d); 8.25 (1H, d); 8.15 (1H, dd); 7.50 (2H, m); 7.15 (3H, m); 6.80 (2H, d); 3.80 (3H, s); 3.60 (4H, m); 3.35 (4H, m); 2.85 (6H, s), 2.50 (2H, m), 2.10 (1H, broad); 1.65 (2H, m). ESI-MS: m/z+H$^+$= 489.87, m/z+Na$^+$=511.60. 1 mmol of product 3 was dissolved in DCM and 1.4 mmol of triethylamine were added. 1.3 mmol of mesyl chloride were slowly dropped and solution stirred at room temperature for 1.5 hrs. TLC (3:2 petroleum ether:ethyl acetate) of reaction mixture showed total con-

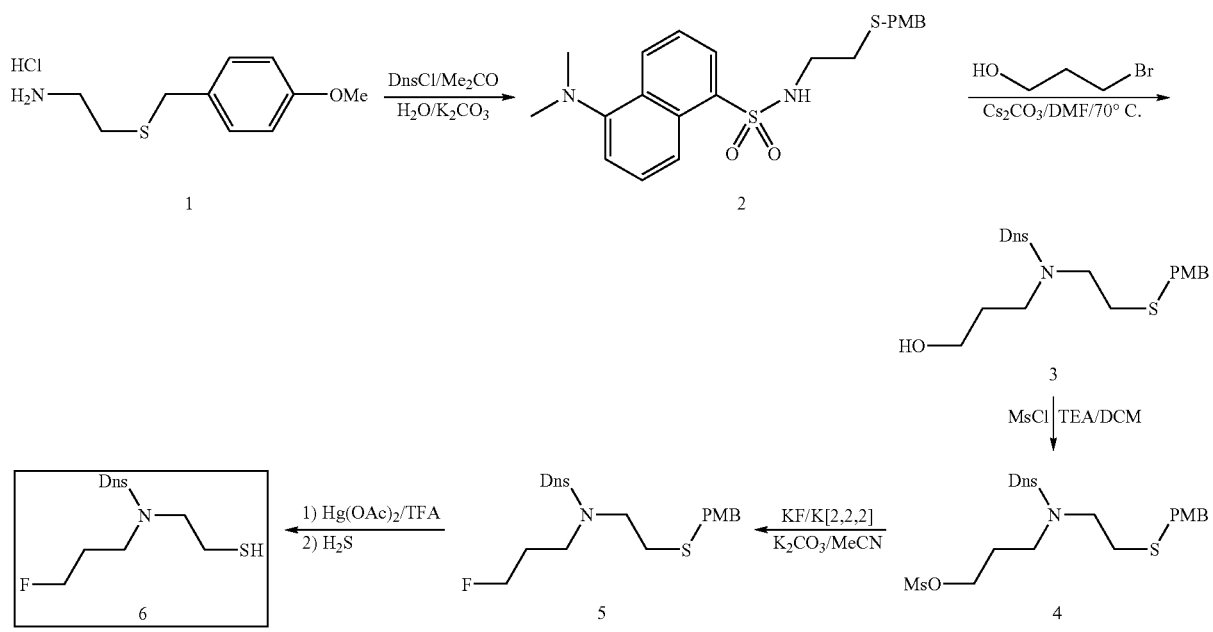

sumption of all starting material and appearance of a new material running above the starting one. Solution mixture was diluted with more DCM, washed with 1M NaHSO$_4$ and 5% NaHCO$_3$, dried over MgSO$_4$ and solvent removed. TLC showed a clean spot at Rf=0.45. Product (4) was used without further purification. Its characterization was as follows: $^1$H-NMR (CDCl$_3$, =ppm): 8.55 (1H, d); 8.25 (1H, d); 8.15 (1H, d); 7.55 (2H, m); 7.20 (1H,d); 7.15 (2H, d); 6.80 (2H, d); 4.10 (2H, t); 3.80 (3H, s); 3.60 (2H, m); 3.35 (4H, q); 2.95 (3H, s), 2.85 (6H, s); 2.50 (2H, t), 1.90 (2H, m). ESI-MS: m/z+H$^+$=567.33, m/z+Na$^+$=589.27.

n-(3-fluoropropyl)-N-(2-PMB-thioethyl)-dansylamide (5): 1 mmol of KF, 1 mmol of Kryptofix [2,2,2] and 0.5 mmol of K$_2$CO$_3$ were dissolved in 10% water in acetonitrile. The solution was evaporated until dryness, residue dissolved in dry acetonitrile and solvent removed again. This process was repeated three more times opening the evaporator into a nitrogen atmosphere. A solution containing 0.2 mmol of product 3 dissolved in dry acetonitrile was added to the dry residue and mixture refluxed for 15 min. Solvent was then removed and residue dissolved in minimal volume of 25% petroleum ether in DCM. Solution was directly applied to a silica gel column and eluted with the above solvents mixture. First yellow fluorescent substance eluted was collected. ESI-MS and $^1$H-NMR was in accordance with desired substance 5. $^{19}$F-NMR (CDCl$_3$, =ppm): −44.50, m. $^1$H-NMR (CDCl$_3$, =ppm): 8.55 (1H, d); 8.25 (1H, d); 8.15 (1H, dd); 7.50 (2H, m); 7.15 (3H,m); 6.80 (2H, d); 4.40 (1H, t); 4.25 (1H, t); 3.75 (3H, s); 3.60 (2H, m); 3.35 (4H, m); 2.95 (3H, s), 2.85 (6H, s); 2.50 (2H, m), 1.80 (2H, m). ESI-MS: m/z+H$^+$=491.72. 0.5 mmol of product 5 were dissolved in 5 ml TFA. 200 µl of anisole were added followed by 1 mmol of mercuric acetate. Solution was kept 15 min. at room temperature and protected from light. Then, TFA was removed by flash evaporation and residue washed with ether. Solid was filtered out, washed with fresh ether and dissolved in methanol. A stream of H$_2$S was bubbled through the solution for 3 min. Solution was stirred for another 5 min. and black precipitate was filtered out through a pad of celite. Sodium acetate was added until neutral pH and solvent removed. Crude was purified by LC eluted with DCM. First yellow fluorescent substance eluted was analyzed to confirm product 6 structure. NST 839 [n-(3-fluoropropyl)-N-(2-thioethyl)-dansylamide (6)] was isolated and characterized as follows: $^{19}$F-NMR (CDCl$_3$, =ppm): −44.70, m. $^1$H-NMR (CDCl$_3$, =ppm): 8.55 (1H, d); 8.30 (1H, d); 8.20 (1H, d); 7.55 (2H, m); 7.20 (1H,m); 6.80 (2H, d); 4.40 (1H, t); 4.30 (1H, t); 3.45 (4H, m); 2.85 (6H, s); 2.65 (2H, q), 1.90 (2H, m); 1.30 (1H, t). ESI-MS: m/z+H$^+$=371.14.

This Example therefore shows the feasibility of attachment of fluorine to NST739, in a method compatible with the conditions used in the "Hot-Box" chemistry of $^{18}$F attachment for clinical PET scan.

Example 2

Selective Binding of NST729 to Cells Undergoing Cell Death Following Middle Cerebral Occlusion (MCA) in Mice An in vivo experiment was conducted in mice to demonstrate the ability of NST729 to identify brain cells undergoing apoptosis following middle cerebral artery (MCA) cauterization in mice.

Experimental Procedures

Studies were carried out in adult male Balb/C mice, weighing 20-25 g. Ischemia was induced by unilateral cauterization of the middle cerebral artery. Briefly, mice were anesthetized, and ischemia was induced through a subtemporal approach. The craniotomy was performed at the level where the MCA crossed the lateral olfactory tract. The dura was carefully opened, the artery exposed and occluded by bipolar diathermy from its origin to the point where it crossed the inferior cerebral vein. All visible branches also were occluded to prevent blood supply by passing. The incision sites were clipped closed and the animal was injected with analgesics and allowed to recover. Twenty-two hours after the middle cerebral artery (MCA) cauterization, BDA (which lack a free thiol residue but is similar apart of this its structure and molecular weight to NST 729 and hence may serve as a control to the necessity of the thiol residues) or NST729 1.4 mg in 200 µl (10% (BDA) and 50% were injected i.v. 2 h before sacrificing the animals. At 24 h from induction of injury, mice were anesthetized, sacrificed, and the brains were removed into liquid nitrogen for further analysis. Frozen sections of 10 µm were prepared. Slices were visualized by a fluorescent microscopy.

Experimental Results

Figure 1:
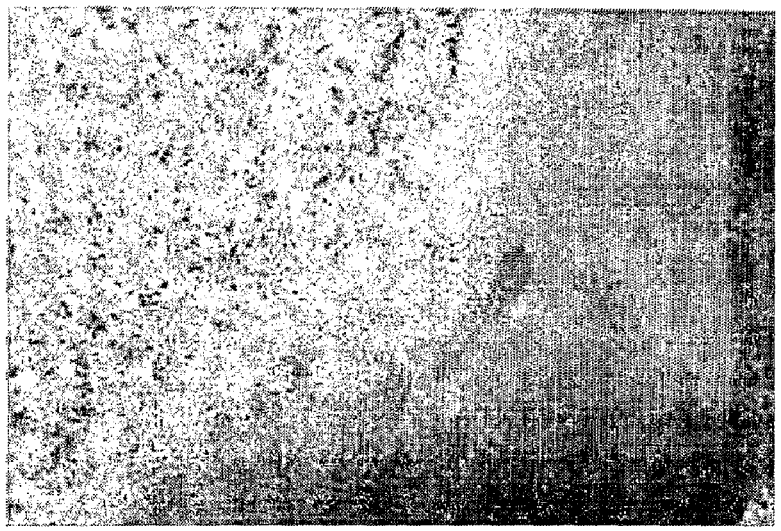
FIG. 1 demonstrates the selective binding of NST 729 to apoptotic cells in the brain in vivo, following middle cerebral artery (MCA) occlusion in mice.
Figure 1:

As can be clearly seen from FIG. 1, the cells in the damaged area showed extensive binding to NST729. The level of binding of NST729, as reflected by the fluorescence intensity, was markedly higher than the level of binding of BDA, which has a similar structure to NST729 but lacks the thiol group. Furthermore, the number of apoptotic events detected by NST729 was significantly higher than the number of cells detected by BDA.

These results show that a free thiol group is an important component in enabling selective binding of the compound to apoptotic cells in the brain.

Example 3

Targeting of Dc In-Vivo to Apoptotic Cells in Tumor, Murine Melanoma

Experimental Procedures

Tumors, and especially aggressive malignancies such as melanoma are characterized, in addition to the abnormal tissue proliferation, also by marked apoptosis of tumor cells. The performance of DC in selective targeting of these apoptotic cells within the tumor was therefore examined. Mice (c57/black; 8 weeks old male mice) were injected subcutaneously bilaterally, in the flank, with murine melanoma-derived B16-F10 cells (ATCC CRL-6475; 10$^5$ cells/mice in a volume of 100 µl). Prior to injection, the cell line was maintained in culture in Dulbecco's modified Eagle's medium (DMEM), supplemented with 4 mM of L-glutamine; 100 units/ml of penicillin; 100 µg/ml of streptomycin; 12.5 units/ml of nystatin and 10% of fetal calf serum (FCS). Tumors were allowed to grow for 14 days, by which they reached a diameter of 5-7 mm.

Dansyl-cysteine (DC), or the control compounds dansyl-glycine or dansyl-serine (2 mg/mouse each in NaPpi buffer, pH. 7.40) was injected intravenously. Two hours later, mice were scarified and the tumors, as well as other organs were taken, and immediately frozen in liquid nitrogen. Frozen sections were then prepared from each of the organs. Uptake of the examined compounds by the tumors or other organs was assessed by fluorescent microscopy.

Experimental Results

Figure 2:
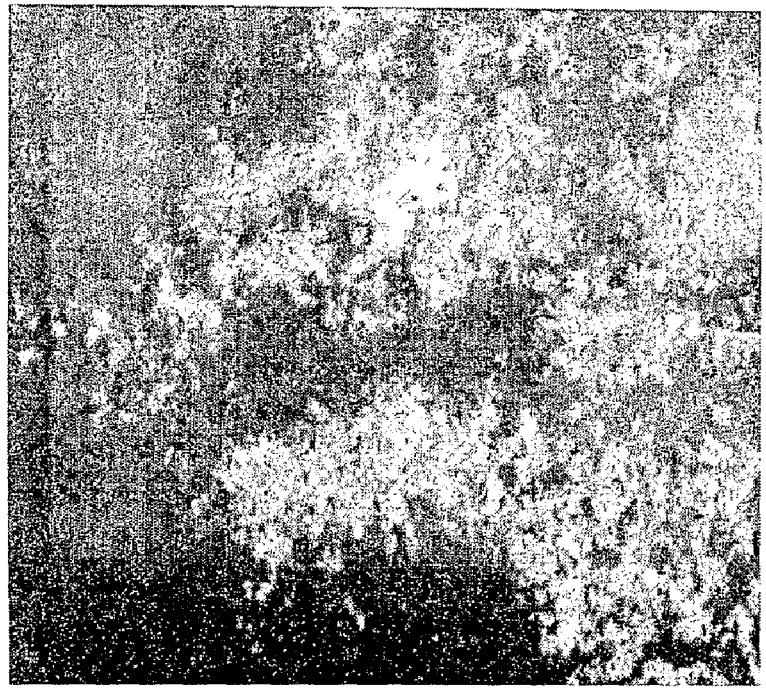
FIG. 2 (A and B) demonstrates the selective binding of DC in vivo to apoptotic cells induced a tumor (FIG. 2A) versus lack of binding to a normal tissue, i.e., the small intestine (FIG. 2B).
Figure 2:
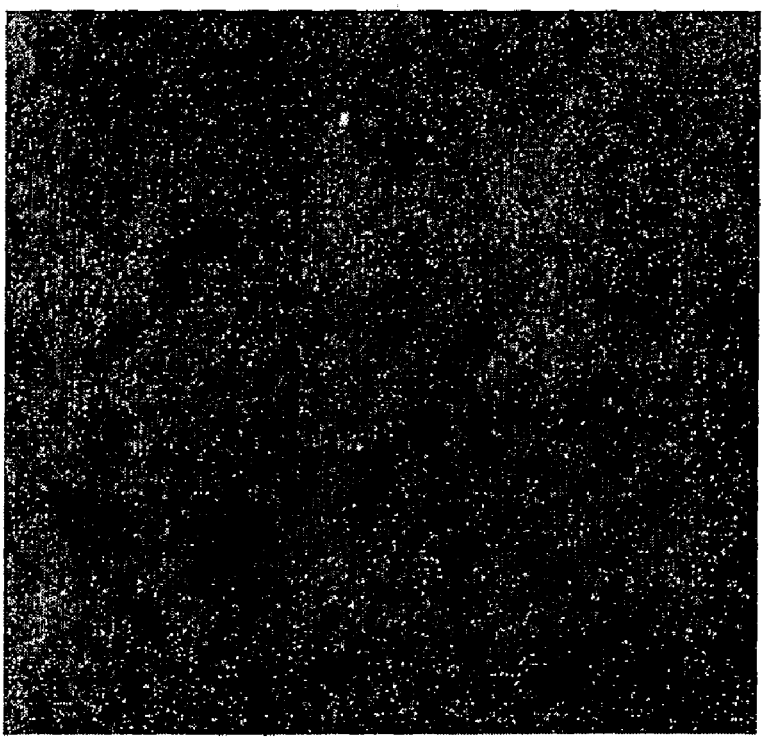

FIG. 2A. shows fluorescent microscopy of the tumor. Extensive binding of DC to numerous tumor cells undergoing cell death can be observed. Demonstrated are also the intracellular accumulation of the compound, and the high level of selectivity, reflected by a marked uptake into the apoptotic cells, while viable tumor cells remain unstained.

This high level of selectivity is also demonstrated in FIG. 2B, showing fluorescent microscopy of small intestine tissue of the same animal, showing lack of binding of the compound to the normal, viable tissue. Similar results were obtained from various other non-target tissues, such as colon, kidney, spleen, muscle and heart.

By contrast, dansyl-glycine and dansyl-serine which have a similar structure to DC but lack a free thiol group did not manifest a significant uptake by neither the apoptotic or the viable tumor cells data not shown.

The results demonstrate the importance of a free thiol group, in entailing the compound selective binding to cells undergoing apoptosis.

Example 4

Detection of Amyloid Plaques in APP Swedish TG2576 Mice Having Double Mutated APP Studies were carried out in one and a half year old APP Swedish TG2576 mice, which have a mutation of APP. BDA (which lacks a free thiol residue) and NST729 were injected i.v., two hours later, mice were anesthetized and brains were removed into liquid nitrogen for further analysis. Frozen section of 10 μm thickness each were prepared, and visualized by fluorescent microscopy.

Experimental Results

Figure 3:
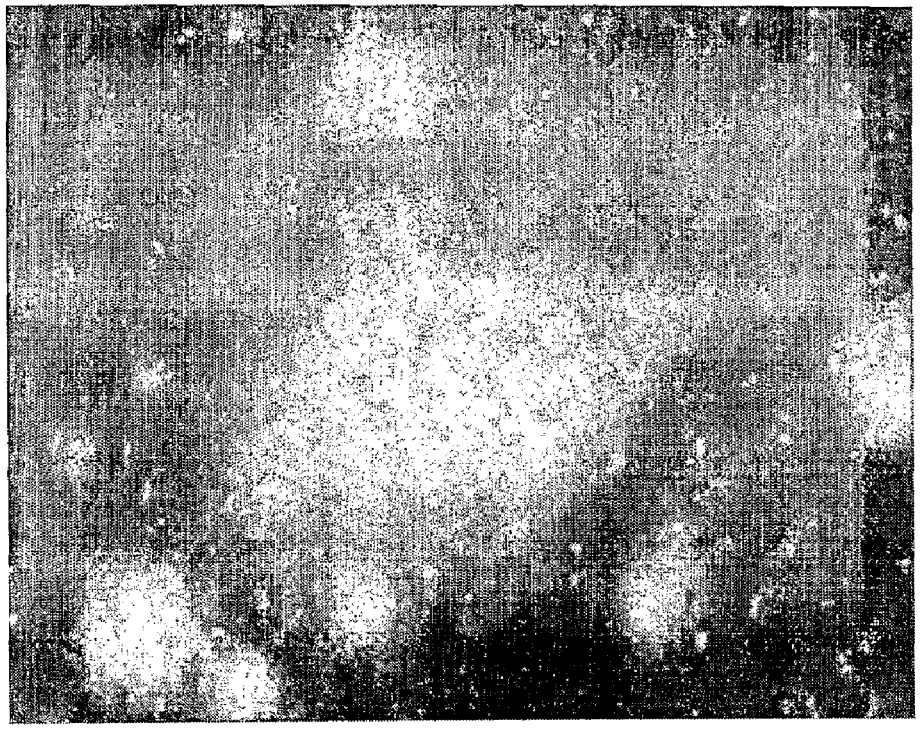
FIG. 3 shows binding of NST729 in vivo to amyloid senile plaques in the brains of transgenic APP TG2576 mice.

As can be clearly seen from FIG. 3, the amyloid plaques were strongly visualized by NST729, while the surrounding brain cells remained unstained. The intensity of binding of NST729 to the plaques was markedly higher than the intensity of binding of the control compound BDA, as assessed by comparative analysis of fluorescence intensity.

The results demonstrate that NST729 can selectively bind to amyloid plaques within the brain, and that the —SH group of the compound has a role in entailing this property.

Example 5

Selective Binding of NST729 In Vivo to Degenerating Neuronal Cells in a Mouse Model of Motor Neuron Disease Studies were carried out in transgenic mice for SOD with point mutation of G93A. NST729 (1.4 mg / animal in 200 μl 50% Cremophor/ trizma-base 0.1M was injected i.v. After two hours, mice were anesthetized and brain +spinal cord were removed into liquid nitrogen for further analysis. Frozen sections of 10 μm thickness were prepared. The slices were visualized by fluorescent microscopy.

Experimental Results

Figure 4:
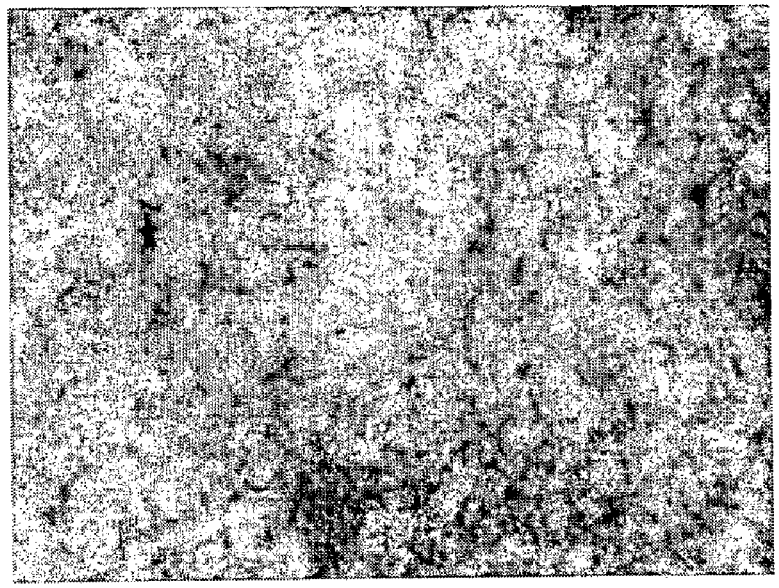
FIG. 4 shows binding of NST729 in vivo to degenerating neuronal cells in a mouse model of motor neuron disease.
Figure 4:
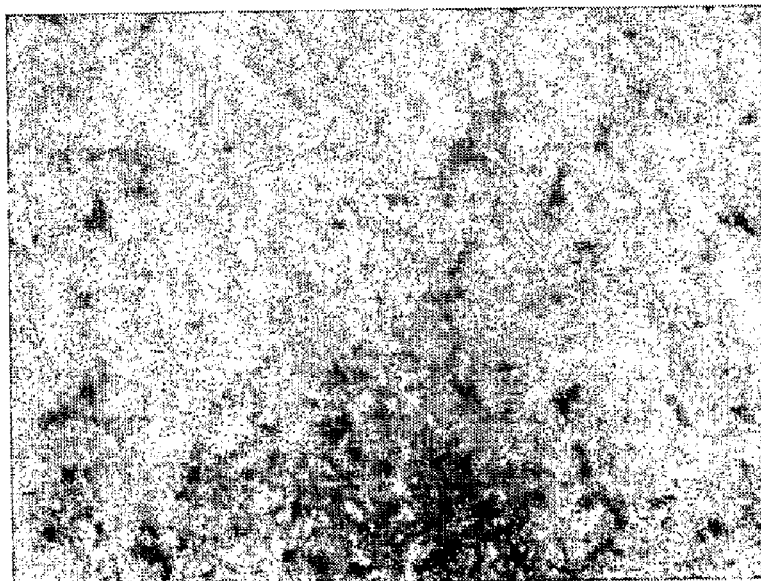

FIG. 4 shows a cross-section through the motor nuclei of the pons. A severe, widespread degenerative process neuronal cells is seen. Predominant is the degenerative process of neuronal axons, with severe deformation, irregularities and thickening of the axonal projections. All these neuropathologies manifested a marked uptake of NST729, while other cells in the same region, as well as cells in other brain regions did not manifest such uptake. This Example therefore clearly shows the potential of NST729, in systemic administration, to specifically target and report on the neuropathological alterations associated with the motor neuron degeneration.

Example 6

Selective Targeting of NST739 to Cells Undergoing Cell Death Following Middle Cerebral Artery Occlusion in Mice An in vivo experiment was conducted in mice, in order to show the performance of NST739 in selective binding to cells undergoing apoptosis, induced by cerebral ischemia due to middle cerebral artery (MCA) occlusion.

Experimental Procedures

Studies were carried out in adult male Balb/C mice, weighing 20-25 g. Cerebral ischemia was induced by unilateral cauterization of the middle cerebral artery. Briefly, mice were anesthetized, and ischemia was induced through a subtemporal approach. The craniotomy was performed at the level where the MCA crossed the lateral olfactory tract. The dura was carefully opened, the artery exposed and occluded by bipolar diathermy from its origin to the point where it crossed the inferior cerebral vein. All visible branches also where occluded to prevent blood supply by passing. The incision sites were clipped closed and the animal was injected with analgesics and allowed to recover. Twenty-two hours after the middle cerebral artery (MCA) cauterization, NST739 or the control compound BDA (1.4 mg/animal each) were injected i.v. At 24 h from the induction of the injury, and two hours after administration of NST739, mice were anesthetized, sacrificed, and brains were removed into liquid nitrogen for further analysis. 10 μl Frozen sections were prepared. The slices were visualized by fluorescent microscopy.

Experimental Results

Figure 5:
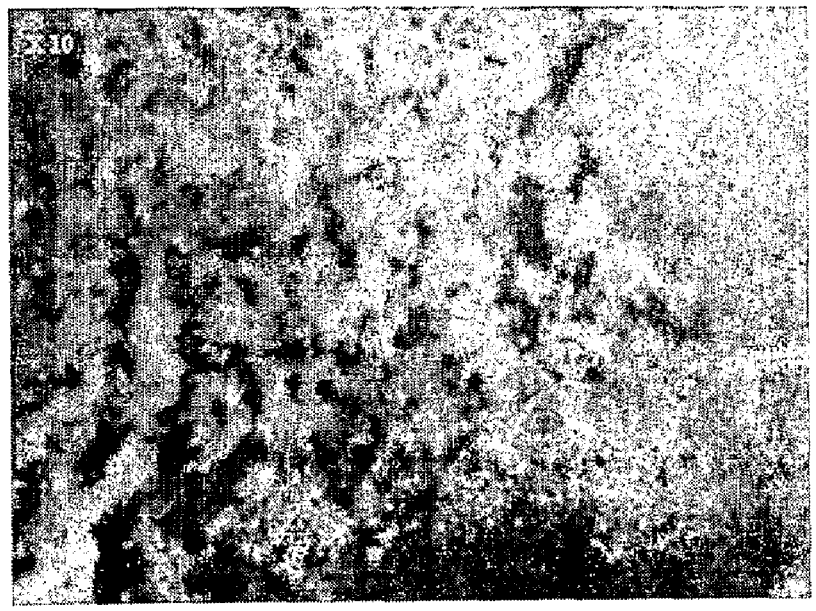
FIG. 5 shows binding of NST739 in vivo to cells undergoing a death process following MCA occlusion in mice.
Figure 5:
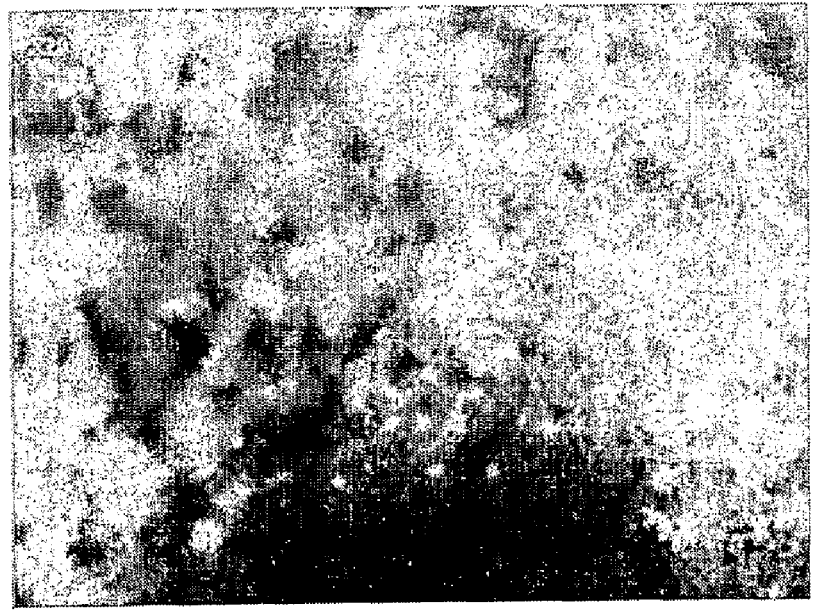

As shown in FIG. 5, cells in the damaged area showed extensive binding to NST739. while cells in other brain regions remained unstained. The level of binding of NST739 as reflected by the fluorescence, was significantly higher for NST739, as compared to the level of binding of BDA which lacks the thiol group.

The results obtained demonstrate the performance of NST739 in selective binding to cells undergoing cell death in the brain, following ischemic injury. The enhanced binding of NST739, in comparison with the binding of DBA shows the importance of the free thiol group in entailing this property of the compound.

Example 7

The Mechanism of Selective Binding of the Compounds of the Invention to Cells Undergoing Disease or Death Process In order to demonstrate the mechanism of action of the compounds of the invention, binding of NST729 to intracellular proteins of a cell undergoing apoptosis will be explained, as is also illustrated in FIG. 6.

The thiol groups of cysteine residues of intracellular proteins of healthy cells are mostly in a reduced state i.e., being free thiols (—SH). This is due to the high cytosolic concentrations of —SH reducing agents. Thus normally, S—S bonds are rarely observed in protein molecules in the cytosol. By contrast, in situations of cell disease, or cells undergoing cell death, e.g., by apoptosis, oxidative stress occurs, and there is loss of intracellular antioxidant mechanisms. This is reflected, among others, by occurrence of disulfide bonds (S—S) between thiol groups of cysteines of intracellular proteins in these cells.

As demonstrated in FIG. 6A, NST729, as representative of the compounds of the invention, comprises a thiol group, capable, in physiological conditions, of being either in an uncharged protonated state, or in a deprotonated state, as a thiolate anion. The unchareed, hydrophobic protonated state allows the compound to traverse cell membranes (as well as the blood brain barrier) and distribute into the intracellular space, while the charged thiolate anion is capable of participating in the thiolate disulfide exchange reaction. As shown in FIG. 6B, in the normal healthy cell, there are not targets for the compound. Therefore, the compound will be washed out of the cell. By contrast, in the apoptotic cell, subjected to oxidative stress and formation of disulfide bonds, the thiolate anion can attack the S—S bond, and replace one of the thiol groups. Due to this reaction, the marker for imaging, comprised within NST729 (the fluorescent dansyl group) now becomes covalently attached to the intracellular protein which cysteine residue took part in the S—S bond (protein A in FIG. 6A). Subsequently, the unbound molecules will be washed out of the cell, leaving only the molecules bound to the sites of S-S bond formation. Due to its properties as an imaging probe (e.g., the fluorescence of the dansyl group of NST729) the marker for imaging of the compounds of the invention may now report on its location: its being in a cell, which is subjected to impairment of the normal cellular redox state, i.e., a cell subjected to oxidative stress, a sick cell and / or a cell undergoing a death process. This report will be now collected and analyzed by imaging equipment, respective of the imaging properties of the probe of the compound (e.g., analysis of fluorescence for dansyl in NST729). Thus the methods of the invention allow the creation of an imaging map of cells undergoing oxidative stress, cell disease or cell death, all cells that will manifest signal, versus healthy viable cells, from which no, or markedly less signal will be obtained.

Example 8

Synthesis of the Neurosense, in Conditions Amenable for Radiolabeling with $^{18}F$, for Imaging Via Positron Emission Tomography (PET)

Various markers for imaging can be utilized with the compounds of the invention. Some of the compounds, such as NST729, comprise a fluorescent probe (e.g., a dansyl group). However, it is desirable to label the compound with a radiolabel that will allow clinical imaging, e.g., via positron emission tomography (PET). For this purpose, a method was developed for the synthesis and labeling with the radio-isotope $^{18}F$ of the compound designated NeuroSense, having the structure set forth in Formula VII:

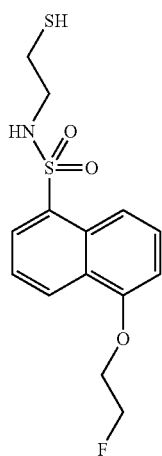

(VII)

The method for the fluorine attachment was developed to accommodate to the conditions and timelines required for the radiochemistry of $^{18}F$ attachment, respective of the half-life of 115 minutes of the $^{18}F$ radio-isotope.

Synthesis of NeuroSense was performed according to the following synthetic scheme:

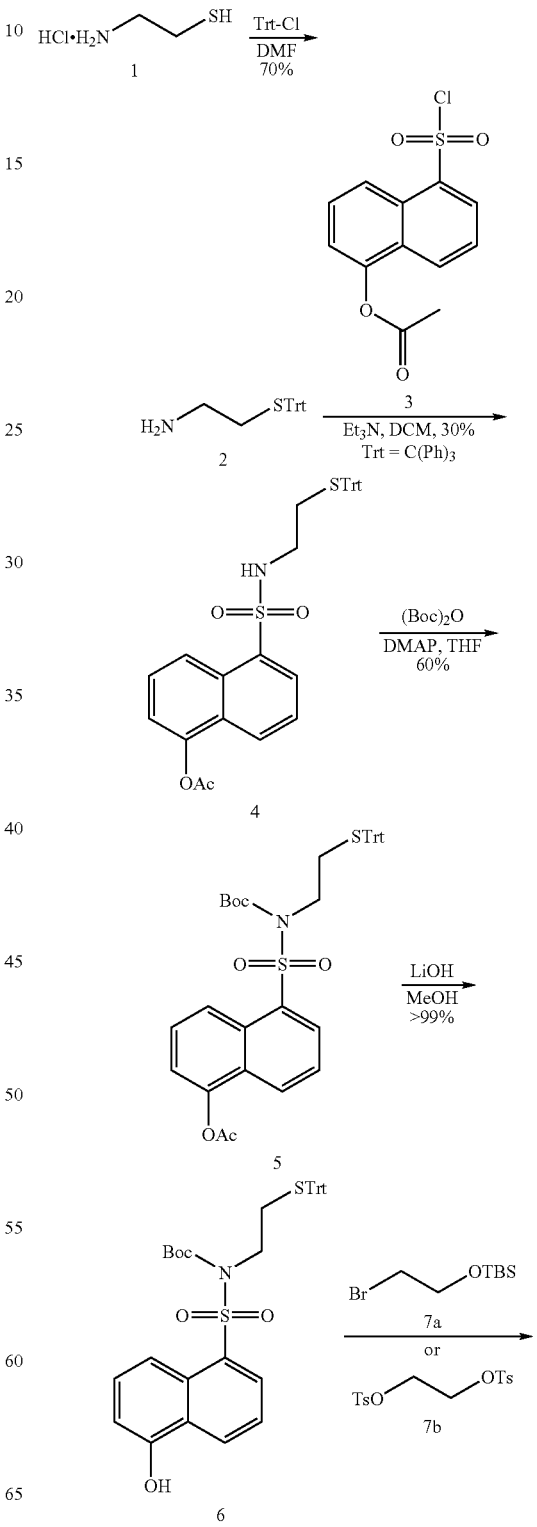

-continued

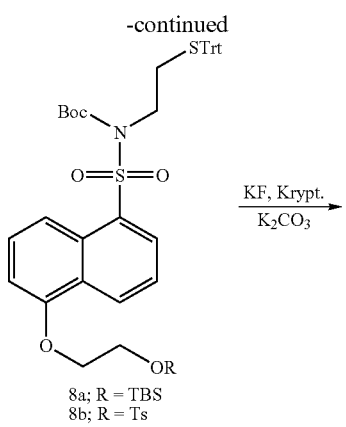

8a; R = TBS
8b; R = Ts

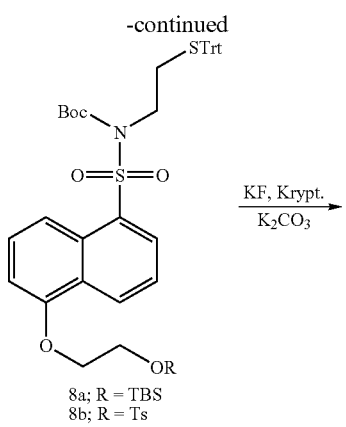

9

NeuroSense

The compliance of this synthetic route with the timelines of the radio-synthesis for $^{18}F$ PET imaging is demonstrated in the following Table 1:

| Procedure | Time |
| --- | --- |
| Kryptofix Reaction in AcCN | 5 min |
| Silica Cartridge Filtration and drying | 10 min |
| Deprotection of 9 | 15 min |
| Purification of NeuroSense | 40 min |

Total synthesis and purification time for NeuroSense is therefore 70 minutes, a time-frame which is well-suited for PET imaging.

What is claimed is:

1. A compound having the structure set forth in formula II:

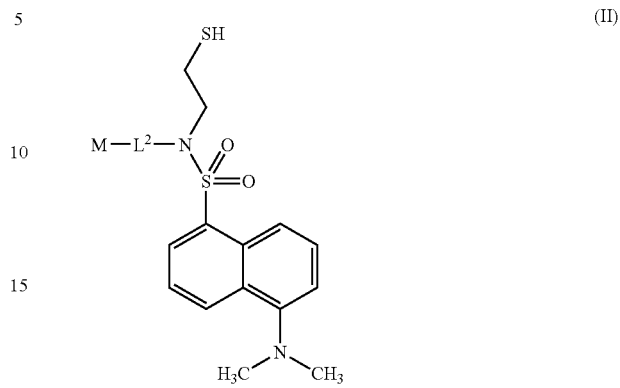

(II)

including pharmaceutically acceptable salts, hydrates, solvates and metal chelates of the compound represented by the structure set forth in formula (II) and solvates and hydrates of said pharmaceutically acceptable salts; wherein M is a marker for imaging and $L^2$ is selected from $C_1$, $C_2$, $C_3$, $C_4$, $C_5$, and $C_6$ linear or branched alkylene linker.

2. A compound according to claim 1, represented by the by the structure set forth in formula IV:

(IV)

including pharmaceutically acceptable salts, hydrates, solvates and metal chelates of the compound represented by the structure set forth in formula (IV) and solvates and hydrates of said pharmaceutically acceptable salts; wherein the n stands for an integer of 2 or 3 and the F atom is the radio-isotope $^{18}F$.

3. A pharmaceutical composition comprising the compound represented by the structure set forth in claim 1, a pharmaceutically acceptable carrier, and a marker for diagnosis.

4. A compound according to claim 2 wherein n=3.

5. A method for detection of a cell undergoing cell death either within a cell population in a cell culture in vitro, or in a tissue of a human or an animal, comprising: (i) administering a compound according to claim 2 to the human or the animal; and (ii) detecting the amount of the compound bound to the cell population in the cell culture or to the tissue of the human or animal; wherein the detection of a significant amount of the compound bound to the cell population in the cell culture or to the tissue of the patient or the animal, indicates the existence of cell death in an examined cell population or the examined tissue in the patient or the animal.

6. A method for detection of a cell undergoing cell death either within a cell population in a cell culture in vitro, or in a tissue of a human or an animal, comprising: (i) administering a compound according to claim 4 to the human or the animal; and (ii) detecting the amount of the compound bound to the cell population in the cell culture or to the tissue of the human or animal; wherein the detection of a significant amount of the compound bound to the cell population in the cell culture or to the tissue of the patient or the animal, indicates the existence of cell death in an examined cell population or the examined tissue in the patient or the animal.

7. The method according to claim 5, wherein the cell death process, or the disease process is associated with oxidative stress.

8. The method according to claim 6, wherein the cell death process, or the disease process is associated with oxidative stress.

9. A pharmaceutical composition comprising the compound represented by the structure set forth in claim 2, a pharmaceutically acceptable carrier, and a marker for diagnosis.

10. A pharmaceutical composition comprising the compound represented by the structure set forth in claim 4, a pharmaceutically acceptable carrier, and a marker for diagnosis.

11. A method for measuring the amount of amyloid plaques in a brain of a human or animal suspected of having Alzheimer's disease comprising the steps of: (i) administering any of the compounds represented by the structures set forth in formulae II or IV and (ii) imaging the human or animal, so as to determine the amount of the compound bound to the amyloid plaques, wherein increased binding indicates that the human or animal has Alzheimer's disease.

12. A method for assessment of the efficacy of an agent in reducing the amount of amyloid plaques, comprising the steps of: (i) administering the agent to an examined human or animal, (ii) administering any of the compounds represented by the structures set forth in formulae II or IV, to the human or the animal and (iii) detecting the amount of plaques by imaging, autoradiography or by histopathology, wherein if the signal intensity is reduced, than the agent is identified as efficacious in reducing the load of the amyloid plaques in the brain of the human or animal.

13. A pharmaceutical composition comprising any one of the compounds represented by the structures set forth in formulae II or IV, a pharmaceutically acceptable carrier, and a marker for diagnosis.

14. A method for measuring the extent of neuro-degeneration in a human or an animal suspected of having a motor neuron disease comprising the steps of: (i) administering any of the compounds represented by the structures set forth in formulae II or IV to the human or the animal; (ii) imaging the human or animal, wherein an increased indicates that the human or animal has a motor neuron disease.

* * * * *